United States Patent
Kreindel

(10) Patent No.: US 6,702,808 B1
(45) Date of Patent: Mar. 9, 2004

(54) DEVICE AND METHOD FOR TREATING SKIN

(75) Inventor: Michael Kreindel, Haifa (IL)

(73) Assignee: Syneron Medical Ltd., Haifa (IL)

( * ) Notice: Subject to any disclaimer, the term of this patent is extended or adjusted under 35 U.S.C. 154(b) by 24 days.

(21) Appl. No.: 09/671,684

(22) Filed: Sep. 28, 2000

(51) Int. Cl.$^7$ ............................................. A61B 18/18
(52) U.S. Cl. .................. 606/9; 606/3; 606/10; 606/23; 606/27; 606/41; 607/88; 607/96; 607/101; 128/898
(58) Field of Search .................... 606/3, 8–10, 20, 606/22–26, 41–50, 131, 27; 607/89, 96–102, 88; 128/898

(56) References Cited

U.S. PATENT DOCUMENTS

| | | | | |
|---|---|---|---|---|
| 5,628,744 A | * | 5/1997 | Coleman et al. | 606/12 |
| 5,683,380 A | | 11/1997 | Eckhouse et al. | |
| 5,735,844 A | | 4/1998 | Anderson et al. | |
| 5,810,801 A | | 9/1998 | Anderson et al. | |
| 5,885,273 A | | 3/1999 | Eckhouse et al. | |
| 5,906,609 A | | 5/1999 | Assa et al. | |
| 5,919,219 A | | 7/1999 | Knowlton | |
| 5,938,657 A | * | 8/1999 | Assa et al. | 606/9 |
| 5,964,749 A | | 10/1999 | Eckhouse et al. | |
| 5,979,454 A | * | 11/1999 | Anvari et al. | 128/898 |
| 6,050,990 A | * | 4/2000 | Tankovich et al. | 606/9 |
| 6,053,909 A | * | 4/2000 | Shadduck | 606/3 |
| 6,090,101 A | | 7/2000 | Quon et al. | |
| 6,104,959 A | * | 8/2000 | Spertell | 607/101 |
| 6,168,590 B1 | * | 1/2001 | Neev | 606/9 |
| 6,210,402 B1 | * | 4/2001 | Olsen et al. | 606/23 |
| 6,235,024 B1 | * | 5/2001 | Tu | 606/41 |
| 6,337,998 B1 | * | 1/2002 | Behl et al. | 607/101 |

OTHER PUBLICATIONS

Welch et al., "Practical Models for Light Distribution in Laser–Irradiated Tissue", *Laser in Surgery and Medicine*, (1987), vol. 6, pp. 488–493.

Gabriel et al., "The dielectric properties of biological tissues: III. Parametric models for the dielectric spectrum of tissues", *Phys. Med. Biol.*, (1996), vol. 41, pp. 2271–2293.

* cited by examiner

*Primary Examiner*—Roy D. Gibson
*Assistant Examiner*—A M Farah
(74) *Attorney, Agent, or Firm*—Browdy and Neimark

(57) ABSTRACT

A system and method for applying, essentially simultaneously, RF energy and optical energy to skin. The system comprises one or more RF electrodes for providing RF energy to the skin; and one or more light sources for providing optical energy to the skin. The method comprises applying, essentially simultaneously, RF energy and light energy to the skin. The method may be used for treating complex targets in the skin.

29 Claims, 5 Drawing Sheets

DEVICE AND METHOD FOR TREATING SKIN

FIELD OF THE INVENTION

The invention relates to methods and devices for treating skin.

BACKGROUND OF THE INVENTION

The term "complex target" is used herein to refer to a feature of the skin having a contrasted or pigmented, component, as well as an uncontrasted, or unpigmented component. For example, a hair is a complex target in which the hair shaft constitutes the contrasted component and the hair follicle constitutes the uncontrasted component. A vascular lesion of the skin is another example of a complex target in which blood constitutes the contrasted component and the walls of the lesion the uncontrasted component. Improving the appearance of the skin often involves the removal of unwanted complex targets.

Photothermolysis has been used for the removal of complex targets. In this method, the target is illuminated with visible or if light that penetrates into the target and is selectively absorbed by the contrasted component. The contrasted component is thus heated, which in turn heats up the uncontrasted component This heating damages the two components of the target, which is ideally destroyed. U.S. Pat. No. 5,735,844 discloses removal of unwanted hairs using radiation having a single wavelength in a pulse of 2 ms to 100 ms. U.S. Pat. No. 5,683,380 discloses hair removal using incoherent filtered light. U.S. Pat. Nos. 5,885,274, 5,964,749 and 5,810,801 disclose skin heating with coherent and non-coherent light sources for smoothing skin and removing age-spots having wavelengths shorter than $1.8\mu$.

In order to be destroyed, the temperature of the target must be raised to about 70° C. without raising the temperature of the epidermis to damaging levels. However, in many cases it is not possible by thermolysis to heat both components of the target to a temperature necessary for destroying the target without heating the surrounding skin to damaging levels. FIG. 1 shows the approximate temperature distribution around a hair after illuminating the hair with a short pulse of visible light. The theoretical curve shown in FIG. 1, as well as the curves shown in FIGS. 2, and 5, referred to below, were obtained using a diffusion equation for light-issue interactions, for example, as disclosed in Welch A. J. et al., Practical Models for light distribution in Laser-Irradiated tissue, in Lasers in Surgery and Medicine, 6:488–493, 1987, and using Maxwell equations for calculating RF current in tissue, for example as disclosed in S. Gabriel et al., The dielectric properties of biological tissues: III. Parametric models for dielectric spectrum of tissues. Phys. Med. Biol. 41: 2271–2293, 1996. Both of the aforementioned publications are incorporated herein by reference in their entirety. When the temperature of the shaft is over 65° C., the average temperature of the follicle is only about 55°. Thus, the optical energy absorbed by the hair shaft is insufficient to adequately heat the follicle. The temperature of the hair cannot be significantly raised beyond these temperatures without raising the temperature of the surrounding skin to damaging levels.

U.S. Pat. No. 5,919,219 discloses using radio frequency (RF) energy for non-selective skin heating. In this method, RF energy is applied to the target that selectively heats the uncontrasted component The uncontrasted component is thus heated, which in turn heats up the contrasted component. However in many cases, it is not possible using RF energy to heat both components of the target to a temperature necessary for destroying the target without heating the surrounding skin to damaging levels. FIG. 2 shows the approximate temperature distribution around a hair after a short pulse of RF energy. When the temperature of the follicle is over 55° C., the temperature of the shaft is only about 50°. The temperature in the skin surrounding the hair is around 40°. The temperature of the hair cannot be significantly raised beyond these temperatures without raising the temperature of the surrounding skin to damaging levels.

SUMMARY OF THE INVENTION

The present invention is based upon the unexpected finding that simultaneous irradiation of a complex target with a combination of RF energy and light (optical energy) can simultaneously heat both the contrasted and uncontrasted components of complex target to a temperature that destroys both components without raising the surrounding skin temperature to damaging temperatures. Without wishing to be bound by a particular theory, it is believed that simultaneous application of RF and optical energies decreases heat loss from the contrasted portion of a target that occurs with optical radiation alone, and similarly decreases heat loss from the uncontrasted portion of the target when RF energy is used alone.

The present invention thus provides a method and apparatus for dermatological treatment of complicated targets of skin in which RF and optical energy are applied, essentially simultaneously, to the skin to heat a target within the skin. By "essentially simultaneously" is meant that the two forms of energy are applied simultaneously, or are applied in rapid succession to one another such that significant cooling of the target does not occur between the first and second applications of energy. The invention may be used for cosmetic treatment of any complicated target such as hair removal, skin rejuvenation and vascular or pigmented lesions. The device includes an applicator with one or more electrode pairs for generation of RF energy and a light source emitting optical energy. Pulsed RF energy applied by the electrodes is applied to the skin either directly or through conductive substance. The frequency of the RF is preferably at least 300 kHz in order to prevent tissue spasms. The visible light may have a single wavelength or several wavelengths that are preferably selected to be optimal for the color of the contrasted component of the target, and are typically in the range of 500 to 1200 nm.

Heat generation during the application of the RF and optical energies is higher near the skin surface. In order to make heating uniform within the skin, the surface is preferably cooled during treatment. The surface may be cooled by applying a cooled substance such as ice or ethanol to the skin or by using a thiermoelectric cooler. The skin is preferably hydrated in order in enhance the penetration of the cooling into the deep layers of the skin, as is known in the art. When the skin is externally cooled at the surface, the RF and optical energy can heat the target to a depth of up to a few millimeters.

The RF electrodes may optionally be used to monitor skin impedance during the treatment. Since increasing skin temperature leads to a change in impedance, monitoring the skin impedance allows the temperature distribution in the skin to be followed so that the parameters of the treatment may be altered to optimize the treatment. The temperature distribution in the skin depends on the delay between the cooling and the application of the RF and optical energies, the selection of pulse parameters. The temperature distribution within the skin may thus be controlled by controlling the delay between the time the cooling is applied, and the time tile RF and optical energy are applied A microprocessor may be used for determining the optimal delay time (t) in response to a selected skin temperature profile. This may be calculated as is known in the art, for example, using the equation $t=d^2/(4A)$, where d is the cooling depth, which in this case is about equal to the thickness of the epidermis (0.1 mm), and A is the skin diffusivity (about $1.4\times10^{-3}$ cm$^2$/sec Alternatively or additionally, the temperature distribution may be controlled by controlling the pulse duration of the RF energy as is known in the art, for example, as disclosed in Ross et al., theoretical considerations in laser hair removal. IN Dermatologic Clinics, W. B. Saunders Company, Volume 17, pages 333–335, 1999.

The invention thus provides a system for applying, essentially simultaneously, RF energy and optical energy to skin comprising:

(a) one or more RF electrodes adapted to provide RF energy to the skin; and (b) one or more light sources adapted to provide optical energy to the skin.

The invention also provides a method for treating skin comprising applying, essentially simultaneously, RF energy and light energy to the skin.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF PREFERRED EMBODIMENTS

Figure 1:
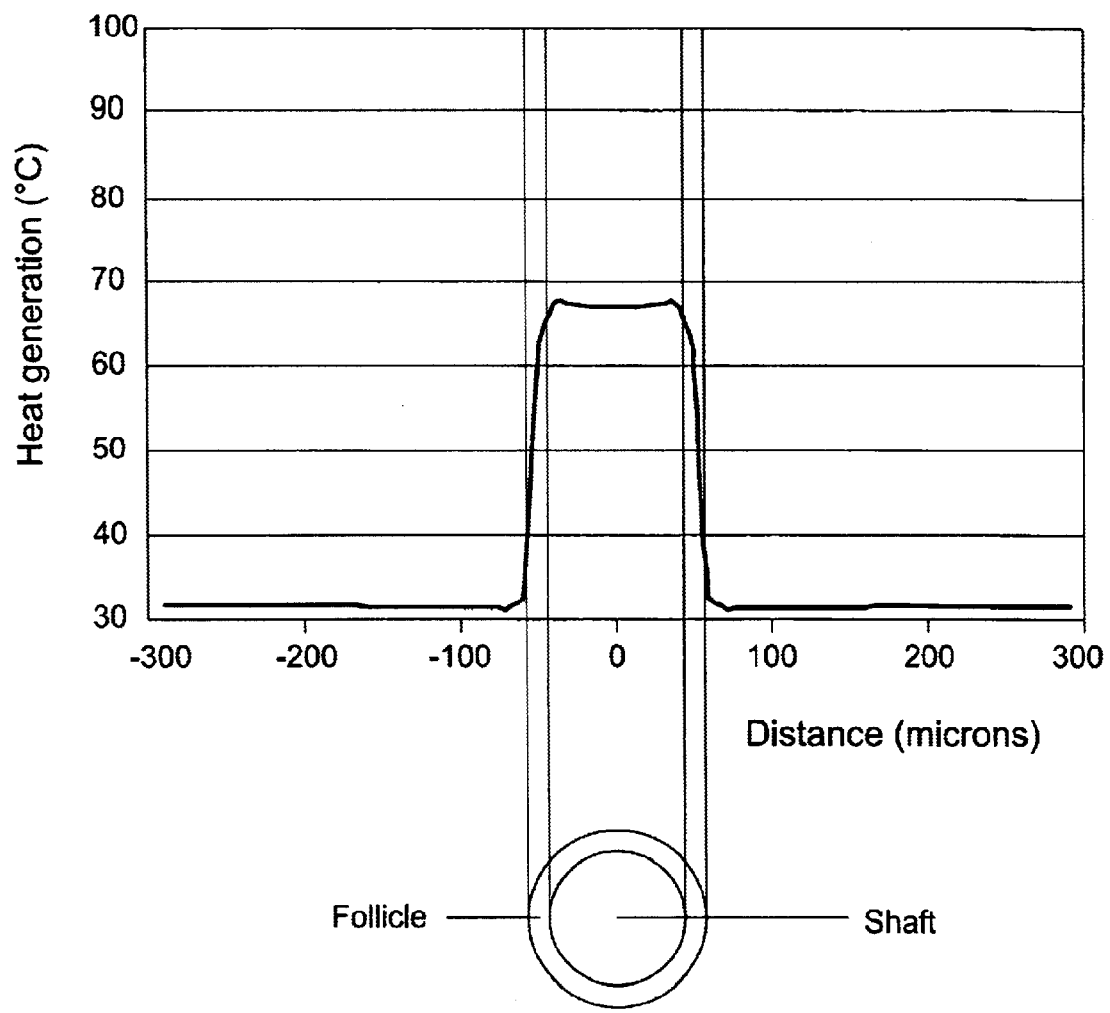
FIG. 1 shows the approximate temperature distribution around a 100 μm hair shaft and follicle following optical energy.
Figure 2:
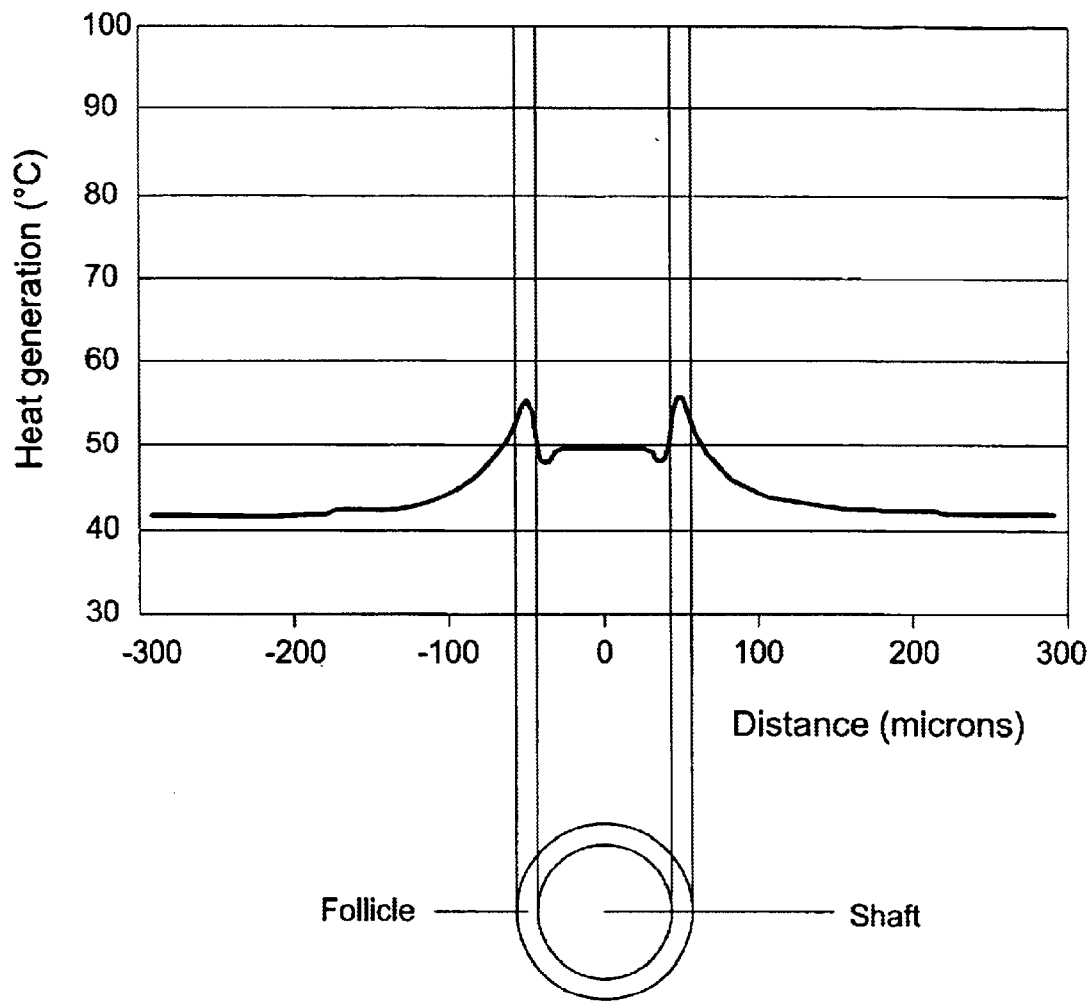
FIG. 2 shows the approximate temperature distribution around a 100 μm hair shaft and follicle following heating by RF.
Figure 3:
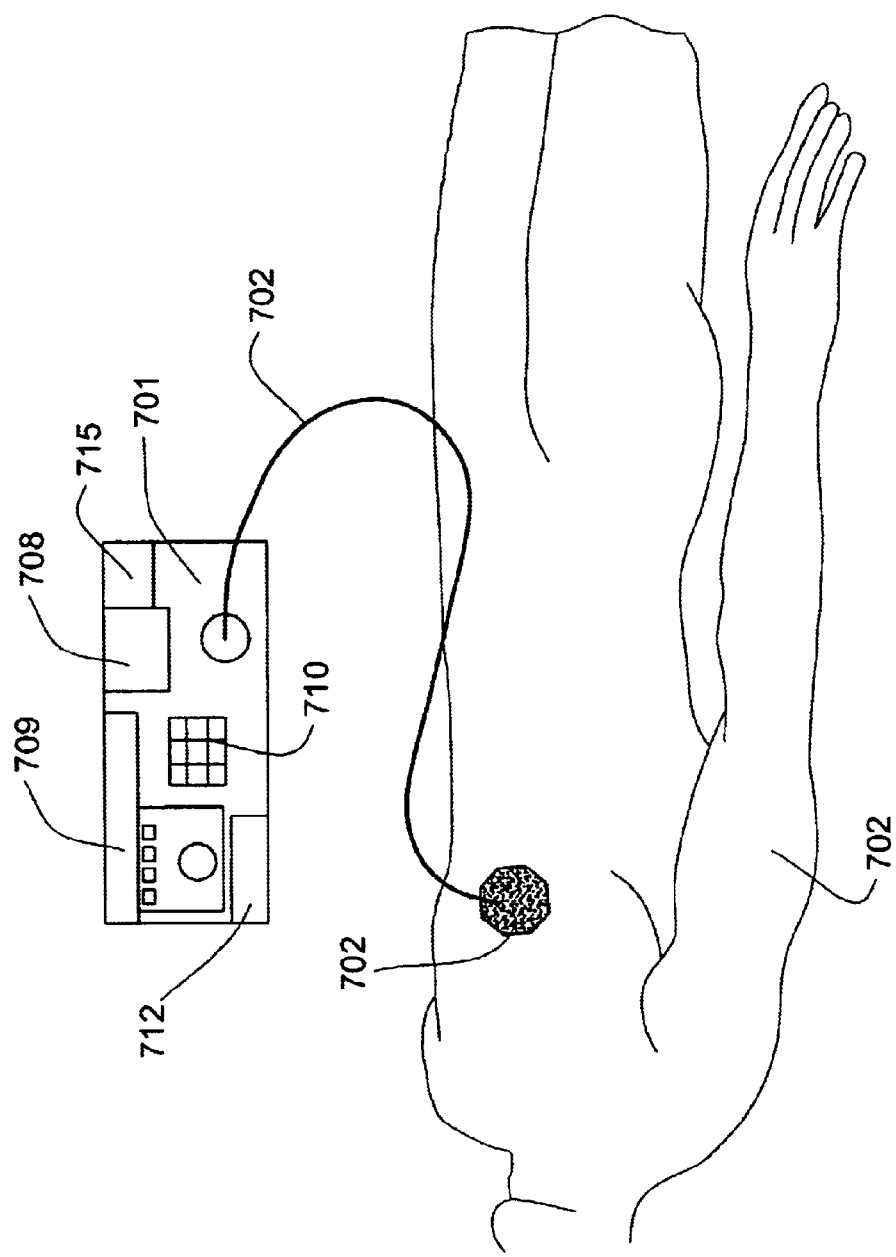
FIG. 3 shows a system for simultaneously applying Rf and optical energy to an individual in accordance with the invention.

Referring now to FIG. 3, a device for applying, essentially simultaneously, RF and optical energies in accordance with the invention is shown. An applicator 703, to be described in detail below, contains a pair of RF electrodes and a light source. The applicator 703 is adapted to be applied to the skin of an individual 705 in the region of a complex target. The applicator 703 is connected to a control unit 701 via a cable 702. The control unit 701 includes a power source 708. The power source 708 is connected to an RF generator 715 that is connected to the RF electrodes in the applicator 703 via wires in the cable 702. The power source 708 is also connected to the light source in the applicator 703 via wires in the cable 702. The control unit 701 contains a refrigeration unit 712 that cools a fluid such as ethanol or water for cooling the applicator 703. The cooled fluid flows from the refrigeration unit 712 to the applicator via a first tube in the cable 702, and flows from the applicator 703 back to the refrigeration unit via a second tube in the cable 702. The control unit 701 bas an input device such as a keypad 710 that allows an operator to input selected values of parameters of the treatment, such as the frequency, pulse duration and intensity of the RF energy or the wavelength and intensity of the optical energy. The control unit 701 optionally contains a processor 709 for monitoring and controlling various functions of the a device. For example, the processor 709 may monitor the electrical impedance between the electrodes in the applicator 703, and determine the temperature distribution in the vicinity of the target. The processor 709 may also determine the parameters of the treatment based upon the impedance measurements.

Figure 4:
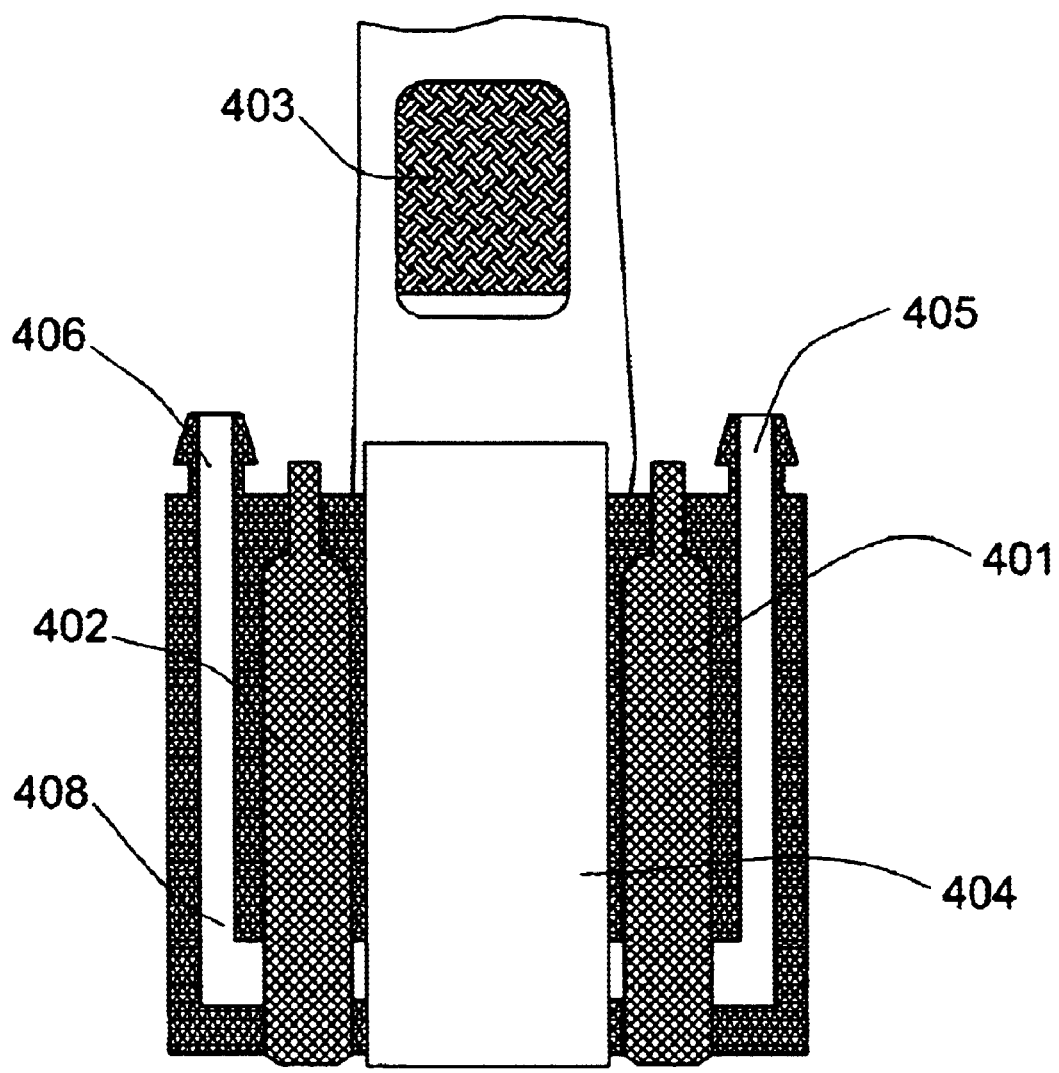
FIG. 4 shows an applicator with two electrodes, light source and cooling system.

FIG. 4 shows the applicator 703 in detail. The applicator contains a pair of electrodes 401 and 402 that apply RF energy to the skin. A light source 403 produces a light spectrum that is delivered to the skin surface by light guide 404. The housing and electrodes are cooled by fluid cooled by the refrigeration unit 712 that flows in a tube 408 between inlet 405 and outlet 406. The inlet 405 and the outlet 406 are connected to the refrigeration unit 712 via the first and second tubes in the cable 702.

Using the system shown in FIG. 3 to apply RF and optical energies to a target having a diameter of at least 2 mm, the following exemplary parameter values may be used:

Frequency of the RF energy: from about 300 kHz to about 100 MHz.

Output power of the RF energy: from about 5 to about 200 W.

Duration of the irradiation: from about 1 to about 500 msec.

Pulse repetition rate: from about 0.1 to about 10 pulse per second.

Intensity of the optical energy: from about 5 to about 100 Joules/cm$^2$.

Pulse duration of optical energy: from about 1 to 200 msec.

Figure 5:
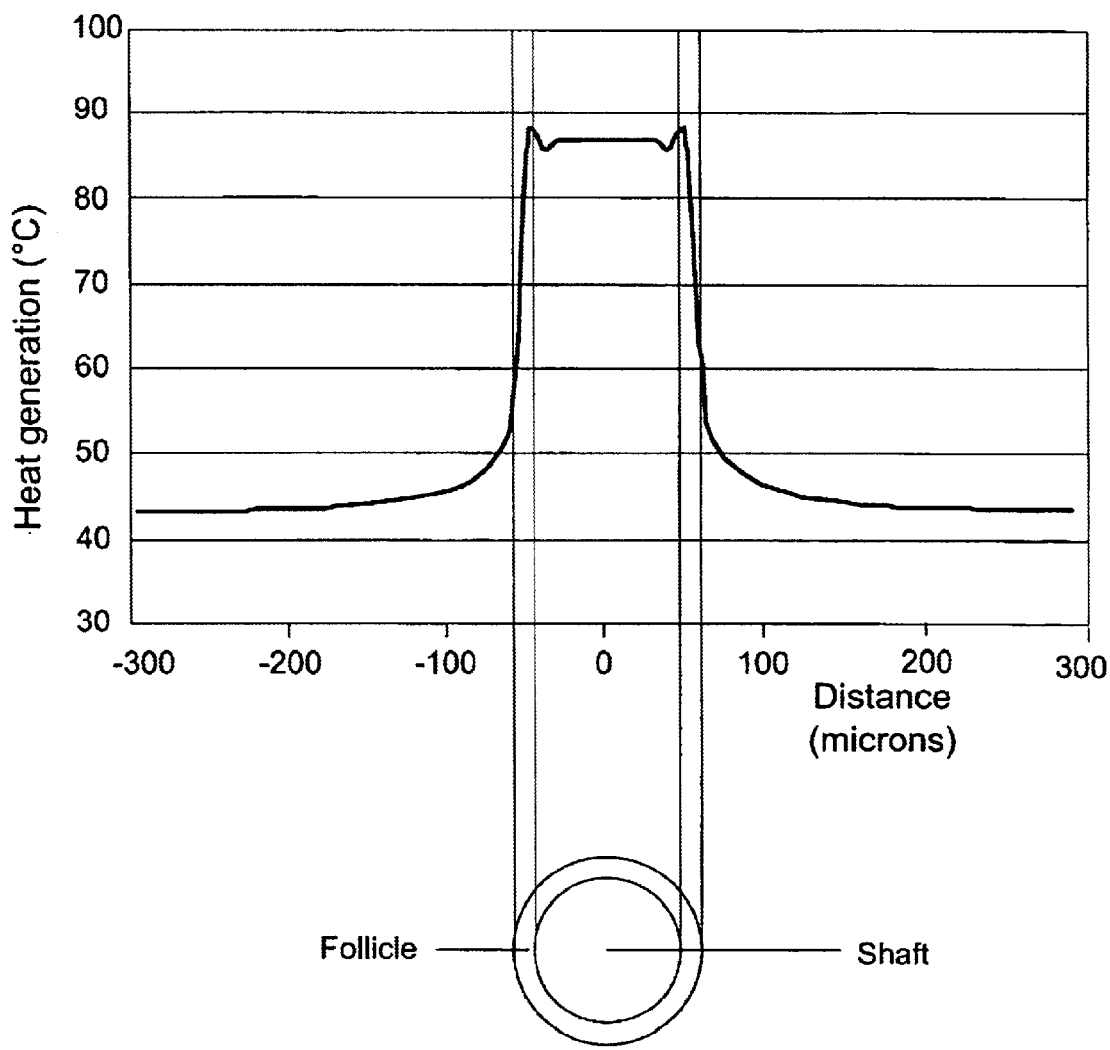
FIG. 5 shows temperature distribution around the 100 micron hair shaft created with combination of optical and RF energy.

FIG. 5 shows the theoretical temperature distribution in a hair that is obtained using the system of FIGS. 3 and 4 with these exemplary parameter values. The temperature in the hair shaft is over 85° C. while the temperature in the surrounding skin is below 45° C.

What is claimed is:

1. A system for treating a skin target area comprising:

(a) one or more RF electrodes adapted to provide RF energy for heating the skin target area; and (b) one or more light sources adapted to provide optical energy having a wavelength not greater than 1200 nm for heating the skin target area, the RF electrodes and the light sources being configured to provide energy essentially simultaneously to the skin target area to heat the entire target area to a temperature that is substantially uniform over substantially the entire target area and that is higher than the temperature that would be created by application of the RF energy alone or the optical energy alone.

2. The system according to claim 1 further comprising a cooling unit adapted to cool the skin.

3. The system according to claim 2 wherein the cooling unit comprises a refrigeration unit cooling a fluid and tubes for allowing the fluid to flow near the skin.

4. The system according to claim 2 wherein the cooling unit comprises a thermoelectric cooler.

5. The system according to claim 1 further comprising a impedance meter for measuring an impedance across one or more of the RF electrode pairs.

6. The system according to claim 5 further comprising a processor configured to determine a heat distribution in the skin based upon one or more impedance measurements.

7. The system according to claim 6 wherein the processor is further configured to determine one or more parameters of the RF energy based upon one or more impedance measurements.

8. The system according to claim 7 wherein the one or more parameters are selected from the group comprising a pulse duration of the RF energy, a frequency of the RF energy, a power of the RF energy, and a delay time between cooling the skin an application of the RF energy.

9. The system according to claim 1 further comprising input, means for determining one or more parameters of the RF energy or the optical energy.

10. The system according to claim 9 wherein the one or more parameters are selected from the group comprising a pulse duration of the RF energy, a frequency of the RF energy, a power of the RF energy, a delay time between, cooling the skin and application of the RF energy, one or more wavelengths of the optical energy, and an intensity of the optical energy.

11. The system according to claim 1 wherein the RF energy has a frequency from about 300 kHz to about 100 MHz, an output power from about 5 to about 200 W, a duration of irradiation from about 1 to about 500 msec, and a pulse repetition rate from about 0.1 to about 10 pulses per second, and the optical energy has an intensity from about 5 to about 100 Joules/cm$^2$ and a pulse duration from about 1 to 200 msec.

12. A method for treating a skin target area comprising applying, essentially simultaneously to the target area, RF energy for heating the target area and light energy having a wavelength not greater than 1200 nm for heating the target area, said step of applying being carried out to heat the entire target area to a temperature that is substantially uniform over substantially the entire target area and that is higher than the temperature that would be created by application of the RF energy alone or the optical energy alone.

13. The method according to claim 12 further comprising cooling the skin.

14. The method according to claim 13 wherein cooling the skin involves cooling a fluid and allowing the fluid to flow near the skin.

15. The method according to claim 13 wherein cooling the skin comprises involves a thermoelectric cooler.

16. The method according to claim 12 further comprising measuring an Impedance across one or more RF electrode pairs.

17. The method according to claim 16 further comprising determining a heat distribution in the skin based upon one or more impedance measurements.

18. The method according to claim 17 further comprising determining one or more parameters of the RF energy based upon, one or more impedance measurements.

19. The method according to claim 18 wherein the one or more parameters are selected from the group comprising a pulse duration of the RF energy, a frequency of the RF energy, a power of the RF energy, a delay time between cooling the skin an application of the RF energy, one or more wavelengths of the optical energy, and an intensity of the optical energy.

20. The method according to claim 12 wherein, a frequency of the RF energy is from about 300 kHz, to about 100 MHz.

21. The method according to claim 12 wherein a duration, of the RF radiation or the optical radiation is from about 1 to about 500 msec.

22. The method according to claim 12 wherein an output power of the RF energy is from about 5 to about 200 W.

23. The method according to claim 12 wherein a pulse repetition rate is from about 0.1 to about 10 pulses per second.

24. The method according to claim 12 wherein an intensity of the optical energy is from about 5 to about 100 Joules/cm$^2$.

25. The method according to claim 12 wherein a pulse duration of optical energy is from about 1 to 200 msec.

26. The method according to claim 12 further comprising hydrating the skin.

27. The method according to claim 12 for use in destroying a complex target in the skin.

28. The method according to claim 27 wherein the complex target is selected from the group comprising a hair and a vascular lesion.

29. The method according to claim 12 wherein the RF energy has a frequency from about 300 kHz to about 100 MHz, an output power from about 5 to about 200 W, a duration of irradiation from about 1 to about 500 msec, and a pulse repetition rate from about 0.1 to about 10 pulses per second, and the optical energy has an intensity from about 5 to about 100 Joules/cm$^2$ and a pulse duration from about 1 to 200 msec.

* * * * *